United States Patent [19]

Rossoff

[11] Patent Number: 4,840,909

[45] Date of Patent: Jun. 20, 1989

[54] METHOD OF PREPARING A SULFONAMIDE-FOOD COLOR ADDITIVE FOR DETECTION OF SULFONAMIDES IN ANIMAL FEEDS AND PHARMACEUTICALS PREPARATIONS

[76] Inventor: Irving S. Rossoff, 515 Springfield Rd., P.O. Box 333, Taylorville, Ill. 62568

[21] Appl. No.: 89,511

[22] Filed: Aug. 26, 1987

Related U.S. Application Data

[63] Continuation of Ser. No. 846,360, Mar. 31, 1986.

[51] Int. Cl.$^4$ ............................................. G01N 33/02
[52] U.S. Cl. ....................................... 436/20; 436/56; 436/92; 436/120; 436/166; 426/231
[58] Field of Search .................. 116/201, 206; 436/56, 436/20, 164, 166, 92, 120; 426/231

[56] References Cited

U.S. PATENT DOCUMENTS 2,712,997  7/1955  Cooley ................................. 426/231
3,438,781  4/1969  MacMillan et al. ................. 426/250

FOREIGN PATENT DOCUMENTS 1418332  12/1975  United Kingdom ................ 426/231

OTHER PUBLICATIONS

Dept. of Health & Human Resources; FDA Mar. 25, 1985.

*Primary Examiner*—Michael S. Marcus
*Attorney, Agent, or Firm*—Senniger, Powers, Leavitt and Roedel

[57] ABSTRACT

A method of preparing a sulfonamide-food color additive for detecting the presence of a compound such as a sulfonamide in animal feeds and pharmaceutical preparations for human or veterinary use involves admixing a minor amount of an approved food color additive with the compound in the presence of water and drying the resulting mixture to the desired form so as to incorporate the food color additive into the water of crystallization or other molecular structure of the compound. Upon being wetted, the resulting compound-food color additive produces a readily detectable color indicative of the presence of the compound. The method is particularly useful for detecting unacceptable levels of sulfonamides in animal feeds.

5 Claims, No Drawings

METHOD OF PREPARING A SULFONAMIDE-FOOD COLOR ADDITIVE FOR DETECTION OF SULFONAMIDES IN ANIMAL FEEDS AND PHARMACEUTICALS PREPARATIONS

This is a continuation of application Ser. No. 846,360, filed Mar. 31, 1986.

BACKGROUND OF THE INVENTION

This invention relates to a method for detecting color as an indicator of the presence of a contaminant or an undesired component in animal feeds and pharmaceutical preparations and, more particularly, to a method for detecting the presence of a sulfonamide or other undesired component in such feeds or pharmaceutical preparations.

As is known, the Food and Drug Administration and the U.S. Department of Agriculture have established acceptable levels for antibiotic sulfonamides ("sulfas"), such as sulfamethazine, in pork. Nevertheless, the problem of illegal sulfa drug residue levels in pork has persisted and it is difficult to monitor the presence of unacceptable levels of sulfas in premixed animal feeds and to clean equipment which has been used in processing feeds with unacceptable levels of sulfas since these compounds cling to metal equipment and readily contaminate other feeds processed therein. According to government regulations, many sulfas may not be added to animal feed since such use may result in residue violations in pork and other meat products. Sulfas in combination with other antibiotics have been approved for use in swine feeds and the approved feed level for sulfas is generally the effective amount hogs can handle without producing illegal residues when a required withdrawal time is observed.

Sulfa violations have heretofore been difficult to detect and there has been no practical and convenient means available for determining whether animal feeds contain even traces of sulfas and/or in amounts which are within acceptable levels. Also, the regulatory agencies involved have not been equipped with techniques for monitoring the adequacy of feed mixing procedures or the cleanliness of equipment to insure that sulfas are maintained at acceptable levels in animal feeds. Similar problems are encountered in the case of other preparations, such as various pharmaceutical preparations, where it is important to insure that certain contaminants or impurities whose presence may be deleterious are not contained in the preparations.

Accordingly, there has been a continuing need for the development of practical and convenient means for detecting and monitoring the presence of sulfonamides and other compounds in animal feeds and pharmaceutical preparations for human or veterinary use and on processing equipment.

SUMMARY OF THE INVENTION

Among the several objects of the invention may be noted the provision of a novel method for detecting the presence of a sulfonamide or other compound in animal feeds and pharmaceutical preparations; the provision of such a method which is relatively simple to practice and which affords a visual colorimetric means for indicating the presence of an undesired contaminant or component in animal feeds or pharmaceutical preparations; and the provision of such a method which permits such undesired contaminants or components to be detected in animal feeds, pharmaceutical preparations, processing equipment and in the meat of animals which have consumed the feeds. Other objects and features will be in part apparent and in part pointed out hereinafter.

Briefly, the present invention is directed to a method for detecting the presence of a compound such as a sulfonamide in animal feeds and pharmaceutical preparations for human or veterinary use which comprises admixing a minor amount of an approved food color additive with said compound in the presence of water and drying the resulting mixture to the desired form of powders, granules or spheres so as to incorporate said food color additive into the water of crystallization or other molecular structure of the said compound whereby, upon being wetted, the resulting compound-food color additive produces a readily detectable color indicative of the presence of said compound.

DESCRIPTION OF THE PREFERRED EMBODIMENTS

In accordance with the present invention, I have now found that the presence of sulfonamides and other compounds in animal feeds and pharmaceutical preparations and on processing equipment can be practically and readily detected by color coding such compounds with minute amounts of approved food color additives under conditions such that the additives become incorporated into the water of crystallization or other molecular structure of such compounds and thereby produce a readily detectable color when the resulting compound-food color additive combination is wetted even where the compound has limited water solubility. The present invention thus permits the color coding of various different sulfonamides, the residues of which in feed, equipment and meat are of great concern to regulatory personnel and, similarly, the invention can be used to color code drug compounds for human or veterinary use where such compounds may be contaminants or undesirable components of a preparation or where it is important to detect whether the level of such compounds in a preparation is acceptable or unacceptable. The color coding and detection method of the invention also provides a useful technique of policing within an industry to combat and baffle "rip-offs" or offending preparations.

Significantly, the invention permits an extremely large amount by weight of a sulfonamide or other compound to be colored by a relatively small amount of approved food color additive. Thus, the weight ratio of color additive to sulfonamide or other compound to be detected may range between 1:1,000 and 1:4,000 and even at these ratios, it has been found that the color appears to be somewhat uniformly distributed throughout the whole mass of sulfonamide or other compound. Moreover, it has been found that there is no separation of the color from the sulfonamide or other compound during physical processing of the combination or in mixing the combination with feed.

In carrying out the invention, the approved food color additive is first admixed with a sulfonamide or other compound in the presence of a small amount of water, and the resulting mixture is then dried for a period of on the order of 3 to 12 hours or longer at a temperature of approximately 100° to 180° F. Other drying conditions such as spray drying, for example, can also be used if desired and other components such as corn starch and corn syrup may be incorporated as bonding agents where it is desired to produce the final combination of the sulfonamide or other compound/food color additive in the form of tablets or boluses. The final product may be milled to any desired particle size (e.g. 1-2 mm.) for average in feed use and the dried product may desirably be produced in various particle forms such as powders, granules or spheres by using techniques known to those in the art.

While the mechanism by which the food color additive becomes incorporated into a sulfonamide or other compound is not completely understood, it is believed that, in the presence of water, the additive becomes chemically incorporated into the water of crystallization or hydration or is somehow intramolecularly incorporated with the compound. In the case of the sulfonamides, the invention can be carried out by adding an FD&C acidic food color such as FD&C Red 40, FD&C Yellow #5 or the like to an aqueous alkali solution of an alkali metal hydroxide (e.g. sodium or potassium hydroxide) and then mixing the resulting solution with a sulfonamide such as sulfathiazole. Alternatively, a sulfonamide such as sulfathiazole is added to a solution of sodium hydroxide (e.g. 70% solution) in an amount sufficient to convert the sulfathiazole acid molecules into sodium sulfathiazole with only enough water (q.s.) present to facilitate easy and rapid mixing, after which the food color additive or coloring agent is added to the solution. In either of these cases, the chemical incorporation is believed to occur by reason of the hydrogen on the sulfonamide linkage ($SO_2NH$) being replaced with sodium. It is also possible that such acidic food color additives react with the amino groups in the sulfonamides. Still further, some other type of complexing mechanism may occur. In any event, whatever the mechanism, the food color additive cannot be physically separated from the sulfonamide or other compound as to which it becomes chemically incorporated, and the resulting food color additive/compound combination presents an optical illusion of molecule to molecule coloring or of having the color uniformly distributed throughout. When prepared as described above and subjected to wetting, the color quickly and readily leaches out or streams forth and provides a clear colorimetric indicator of the presence of the sufonamide or other compound.

In the practice of the invention, any approved food color additive may be employed and, as used herein, that term is intended to embrace the FD&C food colors such as FD&C Red 40, FD&C Blue #1, FD&C Yellow #5 and other FD&C approved colors as well as naturally occurring colors such as riboflavin, beet juice extracts, betanize and other such colors generally regarded as safe for use in human and animal preparations. The objectives and advantages of the invention can also be achieved when a water-soluble food color is incorporated for various prophylatic or therapeutic purposes, e.g. using riboflavin as a yellow coloring agent and vitamin or phenazopyridine as an orange-red coloring agent and urinary antiseptic-analgesic. Thus, these materials and other like materials may be used to color code sulfonamides or other compounds in accordance with the invention.

As previously indicated, the food color additive/compound combination used in the practice of the invention can be milled by conventional procedures without adversely affecting the molecular distribution of the coloring agent. Also, as indicated, the combination can be produced in various particle sizes and in various particle forms such as granules, powder, spheres, beads, tablets, boluses or the like as desired to provide more even mixing with animal feed ingredients of different sizes and to increase the visual monitoring of distribution by increasing or decreasing the number of colored particles per unit of mass without altering the amount of food color additive utilized.

A further feature and advantage of the present invention is that the food color additive/compound combinations referred to may be used in the conventional manner without affecting their therapeutic effectiveness. for example, as shown in detail hereinafter, it has been found that a triple sulfonamide product color coded in accordance with the invention was useful and clinically effective in rhinitis control of hogs and in the treatment of pneumonias and respiratory disease, with the product being color stable.

The invention thus provides a convenient and practical method for detecting the presence of a sulfonamide or other compound in animal feeds and pharmaceutical preparations by enabling the production of a readily detectable color which visually indicates the presence of a sulfonamide or other compound. The invention also permits simple visual inspection to verify adequate mixing in feeds or other carriers. Further, knowing the concentration of the food color in a sulfonamide, for example, and barring the accidental incorporation of a similar coloring agent, one is enabled to use a simple spectrophotometer to yield a quick, inexpensive and reliable field assay for the sulfonamide in feed. Moreover, visually clean surfaces of equipment still contaminated by a color coded compound will automatically stream forth colors when barely misted with water by agricultural inspectors. Granulating of the color coded product reduces the possibility of electrostatic charges keeping the powdered product in contact with mixing, storing or delivering equipment. Similarly, simple spectrophotometer checks could be employed to verify adequate mixing and analysis in multiple ingredient tablets or powders.

The following examples illustrate the practice of the invention.

EXAMPLE 1

A formulation having the following composition was prepared:

| Component | Percent By Weight |
|---|---|
| A mixture of sulfamethazine, sulfathiazole and sulfanilamide | 95.416% |
| Starch (marketed under trade designation "StaRx Starch" by A.E. Staley) | 2.815% |
| FD&C Blue #1 | 0.040% |
| Corn Syrup | 1.730% |

The above proportions of components were used in making batches of approximately 150-200 lbs in weight by a Pony mixer. The FD&C Blue #1 was premixed in approximately 50 ounces of water and then added to the other components. The Pony mixer paddles intimately mixed the color into and onto the particles or powders of material for about 10 minutes. The starch and corn syrup served as bonding agents so that the mixture could be made into the form of tablets, boluses, powder or other forms.

The resulting pasty material was then crumbled or shoveled onto trays and placed in a dry heat oven at a temperature of 140°-160° F. for a period of 8 hours. The material was then milled to appropriate particle size. A portion of the material was screened while still damp and then further dried.

EXAMPLE 2

A formulation having the following composition was prepared:

| Component | Weight |
| --- | --- |
| Sulfanilamide, USP Powder | 45 lb. |
| Sulfathiazole, USP Powder | 30 lb. |
| FD&C Blue #1 | 1 oz. |
| FD&C Yellow #5 (Tartrazine) | 0.5 oz. |

The FD&C food colors were premixed in water and the components were mixed in a Pony mixer for 10 minutes and then granulated with propylene glycol-starch or similar paste binding agent (1 lbs. 14.5 oz.). The amount of water was only sufficient to facilitate easy and rapid mixing. The resultant mixture was run through a Stokes granulator (#4 mesh) and spread on trays. The material was dried at 110°-120° F., and, when dry, was run through a Stokes Oscillator 8 mesh screen. To the resulting granulations in a mixer was added corn starch (26 lbs. 8 oz.), magnesium stearate (1 lb.) and Duponol C (4 lb.). The final material was mixed for 10 minutes.

EXAMPLE 3

A formulation having the following composition was prepared:

| Component | Weight |
| --- | --- |
| Sulfathiazole, USP | 120 lb. |
| Corn Starch Powder | 6 lb. |
| Erythrosine (FD&C Red #3) | 1 oz. |

The components were weighed out and mixed in a Pony mixer for 10 minutes, the food color component having been pre-mixed with a small amount of water. The mixture was granulated with starch paste (1 lb., 7 oz.) and run through a Stokes Oscillator #4 screen. The material was then spread on trays and dried at 120°-130° F. After drying, the material was run through a Stokes Oscillator 8-10 mesh screen. Corn starch (6 lb.), magnesium stearate (8 oz.) and Duponol C (1 lb., 5½ oz.) were then added and the material mixed in a Pony mixer for 10 minutes.

EXAMPLE 4

A formulation having the following composition was prepared:

| Components | Amount |
| --- | --- |
| Urea, USP granular | 92 lb., 4 oz. |
| Sulfanilamide, USP powder | 15 lb., 10 oz. |
| Sulfathiazole, USP powder | 6 lb. |
| Tartrazine (FD&C Yellow #5) | 1 oz. |

The components were weighed out and mixed for 10 minutes in a Pony mixer, the food color component having been pre-mixed with a small amount of water. The mixture was then granulated with starch paste until the color was brought out. The material was put on trays and dried overnight at a temperature of 110°-130° F. The dried material was then put through a Stokes oscillator, 8-10 mesh, and corn starch (5 lb., 8 oz.), boric acid (6 oz.) and stearic acid (12 oz.) were added. The resulting material was mixed for 10 minutes in a Pony mixer.

In each of Examples 1-4, the final product upon being wetted produced a readily detectable color indicative of the presence of the sulfonamide compound contained in the product.

EXAMPLE 5

The formulation of Example 1 was used in clinical trails in swine for the treatment of pneumonias, "flus" and in rhinitis control. 500 grams of the formulation per ton of swine or hog feed was used. Over 15,000 hogs were treated with this feed for 4 days as therapy for pneumonias and respiratory disease. The treatment was found to be safe and effective and the product was observed to be color stable.

In addition, 150 tons of hog feed medicated at the rate of 500 grams of the formulation of Example 1/ton of feed were used to control atrophic rhinitis. A portion was fed to carrier sows to prevent spread of infective organisms to their baby pigs and most of the feed was given continuously to suckling and early weaned (3-4 weeks of age) pigs. This is equivalent to the continuous consumption of the medicated feed for 45 days by approximately 4,000 piglets. It was found that the therapy was safe and effective.

In view of the above, it will be seen that the several objects of the invention are achieved and other advantageous results attained.

As various changes could be made in the above methods without departing from the scope of the invention, it is intended that all matter contained in the above description [or shown in the accompanying drawings] shall be interpreted as illustrative and not in a limiting sense.

What is claimed is:

1. A method for preparing a sulfonamide-food color additive product for incorporation into an animal feed which product, upon being wetted, produces a visually detectable color indicative of the presence of said sulfonamide, which method consists essentially of admixing a minor amount of an approved food color additive with a sulfonamide in the presence of water, and drying the resulting mixture so as to incorporate said food color additive into said sulfonamide thereby producing a sulfonamide-food color additive product which, upon being wetted, produces a visually detectable color indicative of the presence of said sulfonamide.

2. A method as set forth in claim 1 wherein said sulfonamide is sulfathiazole.

3. A method as set forth in claim 1 wherein the weight ratio of food color additive to said sulfonamide is between the range of approximately 1:1,000 and 1:4,000.

4. A method as set forth in claim 1 wherein said sulfonamide food color additive product is produced in the form of granules, spheres, powders, tablets or boluses.

5. A method as set forth in claim 1 wherein said resulting mixture is dried at a temperature of 100°-180° F.

* * * * *